US006783944B2

(12) United States Patent
Bastian

(10) Patent No.: US 6,783,944 B2
(45) Date of Patent: Aug. 31, 2004

(54) GENETIC CHANGES IN ATYPICAL NODULAR PROLIFERATIONS IN CONGENITAL MELANOCYTIC NEVI

(75) Inventor: Boris C. Bastian, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/039,288

(22) Filed: Jan. 4, 2002

(65) Prior Publication Data

US 2003/0143543 A1 Jul. 31, 2003

(51) Int. Cl.[7] .......................... C07H 21/04; C12Q 1/68
(52) U.S. Cl. ........................ 435/6; 435/91.1; 435/91.2; 536/23.1; 536/24.3; 536/25.32
(58) Field of Search ........................ 435/6, 91.2, 91.1; 536/23.1, 24.3, 25.32

(56) References Cited

U.S. PATENT DOCUMENTS

| | | | |
|---|---|---|---|
| 5,447,841 A | | 9/1995 | Gray et al. |
| 5,830,645 A | | 11/1998 | Pinkel et al. |
| 5,994,523 A | | 11/1999 | Kawakami et al. |
| 6,261,775 B1 | * | 7/2001 | Bastian et al. ............... 435/6 |
| 6,455,258 B2 | | 9/2002 | Bastian et al. |
| 6,465,180 B1 | * | 10/2002 | Bastian et al. ............... 435/6 |

OTHER PUBLICATIONS

Thompson et al. "Cytogenetics of 158 patients with regional or disseminated melanoma." Cancer Genet. Cytogenet. vol. 83, No. 2, pp. 93–104, Sep. 1995.*
Wettengel et al "Differentiation between Spitz nevi and malignant melanomas by interphase FISH", Int. J. of Oncology, vol. 14, pp. 1177–1183, 1999.
De Witt et al "DNA in situ Hybridization as a Diagnostic tool in the discrimination of melanoma and spitz naevus" J. of Pathology, vol. 173, pp. 227–233, 1994.
Bastian et al. "Chromosomal Gains and Losses in Primary Cutaneous Melanomas Detected by CGH" Cancer Research, vol. 58, pp. 2170–2175, May 1998.
Healy et al. "Allelotypes of Primary Cutaneous Melanoma and Benign Melanocytic Nevi" Cancer Research, vol. 56, pp. 589–593, Feb. 1996.
Lichter et al. "Delinieation of individual human chromosomes in metaphase and interphase cells by in situ suppression hybridization using recombinant DNA libraries" Hum Genet. vol. 80, pp. 224–234, 1988.
Matson et al. "Biopolymer Synthesis on Polypropylene Supporst: Oligonucleotide Arrays" Analytical Biochemistry, vol. 224, pp. 110–116, 1995.

Wang et al. "COT–1 banding of human chromosomes using FISH with Cy3 labeling" Jpn. J. Human Genet. vol. 40, pp. 243–252, 1995.
Thompson et al., "Cytogenetics of 158 Patients with Regional or Disseminated Melanoma: Subset Analysis of Near–diploid and Simple Karyotypes" Cancer Genet. Cytogenet. 83: 93–104 (1995).
Winokur et al. "Evaluation of DNA Ploidy in Dysplastic and Spitz Nevi by Flow Cytometry", J. Cutan Pathol. 17: 342–347 (1990).
Products for Life Science Research, 2000–2001, Sigma–Aldrich, pp. 170 and 322.
Speicher et al. "Chromosomal gains and losses in uveal melanomas detected by comoparative genomic hybridization" Cancer Research. 1994, 54: 3817–3823.
Day et al., "Malignant melanoma Prognostic Factors 3: Surgical Margins," J. Dermatol. Surg. Oncol. 9:797–801 (1983).
Heenan, "A Centimeter There, a Centimeter There: Does it Matter?" Am. Acad. Dermatol. 35: 281–2 (1996).
Huang et al., "Flurescence in situ Hybridization Evaluation of Chromosome Deletion Patterns in Prostate Cancer," Amer. J. Pathology 149(5): 1565–1573 (Nov. 1996).
Kallioniemi et al., "Comparative Genomic hybridization for Molecular Cytogenic analysis of Solid Tumors," Science 258: 818–21 (1992).
Mishima et al., "Acral Lentiginous melanoma and its Precursor–Heterogeneity of Palmo–Plantar Melanomas," Pathology 17: 258–65 (1985).
Wingo, et al., "Cancer Incidence and Mortality, 1973–1995," Cancer 82: 1197–207 (1998).
Xu et al., "Detection of 11q13 Amplification as the Origin of a Homogeneously Staining Region in Small Cell Lung Cancer by Chromosome Microdissection," Genes, Chromosomes & Cancer 17: 172–178 (1996).
Bastian et al., "Gene Amplifications Characterize Acral Melanoma and Permit the Detection of Occult Tumor Cells in the Surrounding Skin", Cancer Research 60: 1968–1973 (2000).

* cited by examiner

Primary Examiner—Gary Benzion
Assistant Examiner—Jeanine Goldberg
(74) Attorney, Agent, or Firm—Townsend and Townsend and Crew LLP

(57) ABSTRACT

The invention provides methods of distinguishing benign growths arising from congenital melanocytic nevi from malignant melanoma. The methods comprise detecting a change in chromosome number that is specifically associated with benign growths. These changes include a gain of chromosome 10, a gain of chromosome 11, and a loss of chromosome 7.

15 Claims, 3 Drawing Sheets

GENETIC CHANGES IN ATYPICAL NODULAR PROLIFERATIONS IN CONGENITAL MELANOCYTIC NEVI

BACKGROUND OF THE INVENTION

The melanocyte can give rise to a number of morphologically different tumors. Most of them are biologically benign and are referred to as melanocytic nevi. Examples of melanocytic nevi are congenital nevi, Spitz nevi (including pigmented spindle cell nevi, which are regarded as a subtype of Spitz nevi), dysplastic or Clark's nevi, blue nevi, lentigo simplex, and deep penetrating nevus.

Patients with congenital melanocytic nevi (CMN) have an increased risk of developing melanoma. Whereas in small— (<1.5 cm) and intermediate-sized CMN (1.5–20 cm) the risk seems to be low (Rhodes, A. R., *Med Clin North Am.,* 70:3–37 (1986); Sahin, S. et al., *J Am Acad Dermatol.,* 39:428–33 (1998)), large CMN (>20 cm) carry a 5–15x times increased future risk to develop melanoma and rarely, other neural crest derived malignancies ((Swerdlow, A. J. et al., *J Am Acad Dermatol.,* 32:595–9 (1995); Ruiz-Maldonado, R. et al., *J Pediatr.,* 120:906–11 (1992); Quaba, A. A. and Wallace, A. F., *Plast Reconstr Surg.,* 78:174–81 (1986); Gari, L. M. et al., *Pediatr Dermatol.,* 5:151–8 (1988); Egan, C. L. et al., *J Am Acad Dermatol.,* 39:923–32 (1998); Bittencourt, F. V. et al., *Pediatrics,* 106:736–41 (2000); DeDavid, M. et al., *J Am Acad Dermatol.,* 36:409–16 (1997); Marghoob, A. A. et al., *Arch Dermatol.,* 132:170–5 (1996)).

Melanoma refers to malignant neoplasms of melanocytes. Its proper diagnosis and early treatment is of great importance because advanced melanoma has a poor prognosis, but most melanomas are curable if excised in their early stages. Although, in general the histopathological diagnosis of melanoma is straightforward, there is a subset of cases in that it is difficult to differentiate melanomas from benign neoplasms of melanocytes, which have many variants that share some features of melanomas (LeBoit, P. E. Stimulants of Malignant Melanoma: A Rogue's Gallery of Melanocytic and Non-Melanocytic Imposters, In *Malignant Melanoma and Melanocytic Neoplasms,* P. E. Leboit, ed. (Philadelphia: Hanley & Belfus), pp. 195–258 (1994)). Even though the diagnostic criteria for separating the many simulators of melanoma are constantly refined, a subset of cases remains, where an unambiguous diagnosis cannot be reached (Farmer et al., Discordance in the Histopathologic Diagnosis of Melanoma and Melanocytic Nevi Between Expert Pathologists, *Human Pathol.* 27: 528–31 (1996)).

During the neonatal period several types of melanocytic tumors can develop within CMN, many of which are thought to be distinct from melanoma (DeDavid, M. et al., *J Am Acad Dermatol.,* 36:409–16 (1997)). These can be small to large, occasionally involving up to 50% of the trunk, and can grow very fast and ulcerate (Clark, W. H. et al., *Pathology of the Skin,* 1st edition, pp. 729–35, New York, McGraw-Hill (1990)). Most of these tumors have a benign course and tend to regress after a period of rapid growth. However, because true melanoma can occur in the neonate, the development of any secondary proliferation in a CMN is of significant concern.

These lesions can be extremely difficult to classify histologically. Four different histological patterns of proliferations in CMN during the neonatal period have been described (Clark, W. H. et al., *Pathology of the Skin,* 1st edition, pp. 729–35, New York, McGraw-Hill (1990)): 1) simulants of superficial spreading melanoma, in which the epidermis and superficial dermis contain large epitheloid melanocytes, sometimes with pagetoid spread in the epidermis; 2) simulants of nodular melanoma with a nodular proliferation of large melanocytes with uniform nuclei in the dermis; 3) cases described as "proliferative neurocristic hamartoma", characterized by a deep dermal or subcutaneous proliferation with a variety of forms of neural or mesenchymal differentiation; and 4) true melanoma, most of which show small blast-like melanocytes with hyperchromatic nuclei, scant cytoplasm and a high mitotic rate.

The current invention is based on the discovery that chromosomal aberrations are common in atypical nodular proliferations and further, are absent from conventional congenital nevi. The aberrations are predominantly numerical changes, in contrast to those identified in melanoma, in which structural chromosomal aberrations are found in the vast majority of cases. These findings are useful in the classification of histopathologically ambiguous cases.

BRIEF SUMMARY OF THE INVENTION

The current invention provides a method of typing a growth arising in association with a congenital nevus, the method comprising providing a skin tumor sample from a patient and detecting a change in chromosome number in a nucleic acid sample from the skin tumor sample. The change in chromosome number is typically a gain of chromosome 10, a gain of chromosome 11, or a loss of chromosome 7. The presence of one or more of these changes in the skin tumor sample types a lesion as a benign growth. Similarly, the absence of changes in chromosomal aberrations that are frequently associated with melanoma, types the skin tumor sample as a benign growth.

In one embodiment, the detection step comprises contacting a nucleic acid sample from the patient with a probe which selectively hybridizes to a target polynucleotide sequence on a chromosome selected from the group consisting of chromosome 10, chromosome 11, and chromosome 7; wherein the probe is contacted with the sample under conditions in which the probe binds selectively with the target polynucleotide sequence to form a stable hybridization complex; detecting the formation of the hybridization complex; and detecting a change in chromosome number, the change selected from the group consisting of a gain of chromosome 10, a gain of chromosome 11 and a loss of chromosome 7.

The nucleic acid sample can be, for example, an interphase nucleus or a metaphase cell. The probe is often labeled with a fluorescent labeled, but can also be labeled with other labels such as digoxigenin or biotin. Often, the probe is bound to a solid substrate and further, can be a member of an array. In some embodiments, the probe is a centromeric probe.

The methods of the invention can also comprise a further step of contacting the nucleic acid sample with a reference probe that binds selectively to a chromosome that does not undergo changes in chromosome number in these lesions. Such reference probes include, e.g., probes to chromosomes 1, 2, 4, 12, 13, 14, and 19.

Additionally, the methods of the invention can comprise a step of blocking the hybridization capacity of repetitive sequences in the nucleic acid sample. For example, unlabeled blocking nucleic acids such as comprising repetitive sequences, such as Cot-1 DNA, are contacted with the sample.

Definitions

To facilitate understanding the invention, a number of terms are defined below.

The terms "melanoma" or "cutaneous melanoma" refer to malignant neoplasms of melanocytes, which are pigment cells present normally in the epidermis and sometimes in the dermis. There are four types of cutaneous melanoma: lentigo maligna melanoma, superficial spreading melanoma (SSM), nodular melanoma, and acral lentiginous melanoma (AM). Melanoma usually starts as a proliferation of single melanocytes at the junction of the epidermis and the dermis. The cells first grow in a horizontal manner and settle an area of the skin that can vary from a few millimeters to several centimeters. As noted above, in most instances the transformed melanocytes produce increased amounts of pigment so that the area involved can easily be seen by the clinician.

The term "melanocytic neoplasm" refers to an accumulation of melanocytes that can undergo a benign, locally aggressive, or malignant course. "Melanocytic neoplasm" encompasses both benign melanocytic neoplasms, "nevi", and malignant melanocytic neoplasms, "melanoma".

"Congenital melanocytic nevi" refer to moles that are present at birth or arise shortly thereafter. Often, such nevi can grow rapidly. Rapidly growing nodules occasionally arise in these nevi during the neonatal period. Histologically, the nodules often present as atypical nodular proliferation of high cellularity, nuclear atypia and demonstrate and increased proliferation rate. A "growth arising from a congenital nevus" refers to an area of proliferation in a nevus. Using current histological criteria it is often difficult or impossible to classify these growth as either benign or malignant.

The terms "tumor" or "cancer" in an animal refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. "Tumor" includes both benign and malignant neoplasms.

As used herein, a "numerical aberration" refers to a change in number of a whole chromosome compared to normal, e.g., a gain of chromosome 10 refers to a gain of the entire chromosome. A "structural aberration" refers to a change in the structure of a chromosome. "Structural aberrations" includes changes in copy number of chromosomal regions, e.g., changes in copy number of a chromosomal arm or subregions of a chromosomal arm, as well as chromosomal rearrangements such as translocations, insertions, deletions, and other rearrangements.

The phrase "typing" or "detecting" a neoplasm refers to the determination whether the neoplasm is, or has a high probability of being, a certain class of neoplasm. Classification can be based on whether the neoplasm is benign or malignant, or type of nevus, e.g., a congenital nevus. "Typing" or "detecting" can also refer to obtaining indirect evidence regarding the likelihood of the presence of a benign growth or melanoma in the patient. Detection of a benign growth versus a melanoma can be accomplished using the methods of this invention alone, or in combination with other methods or in light of other information regarding the state of health of the patient.

The terms "hybridizing specifically to", "specific hybridization", and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, Ch. 2,* "Overview of principles of hybridization and the strategy of nucleic acid probe assays," Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell (2001) *Molecular Cloning: A Laboratory Manual* (3rd ed.) Vol. 1–3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The term "labeled with a detectable label", as used herein, refers to a nucleic acid attached to a detectable composition, i.e., a label. The detection can be by, e.g., spectroscopic, photochemical, biochemical, immunochemical, physical or chemical means. For example, useful labels include $^{32}P$, $^{35}S$, $^3H$, $^{14}C$, $^{125}I$, $^{131}I$; fluorescent dyes (e.g., FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, digoxigenin, or haptens and proteins for which antisera or monoclonal antibodies are available. The label can be directly incorporated into the nucleic acid, peptide or other target compound to be detected, or it can be attached to a probe or antibody that hybridizes or binds to the target. Label can be attached by spacer arms of various lengths to reduce potential steric hindrance or impact on other useful or desired properties. See, e.g., Mansfield, *Mol Cell Probes* 9: 145–156 (1995). In addition, target DNA sequences can be detected by means of the primed in situ labeling technique (PRINS) (Koch et al., *Genet. Anal. Tech. Appl.* 8: 171–8, (1991)). The sensitivity of the detection can be increased by using chemical amplification procedures, e.g., by using tyramide (Speel et al., *J. Histochem. Cytochem.* 45:1439–46, (1997)).

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189–197. Other synthetic backbones encompasses by the term include methyl-phosphonate linkages or alternating methylphosphonate and phosphodiester linkages (Strauss-Soukup (1997) *Biochemistry* 36: 8692–8698), and benzylphosphonate linkages (Samstag (1996) *Antisense Nucleic Acid Drug Dev* 6:153–156). The term nucleic acid is used interchangeably with gene, cDNA, mRNA, oligonucleotide primer, probe and amplification product.

The term a "nucleic acid array" as used herein is a plurality of target elements, each target element comprising one or more nucleic acid molecules (probes) immobilized on one or more solid surfaces to which sample nucleic acids can be hybridized. The nucleic acids of a target element can contain sequence(s) from specific genes or clones, e.g. from specific regions of chromosomes 7, 10, or 11. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 $\mu$m to about 3 mm, preferably between about 5 $\mu$m and about 1 mm. The target elements of the arrays may be arranged on the solid surface at different densities. The target element densities will depend upon a number of factors, such as the nature of the label, the solid support, and the like. One of skill will recognize that each target element may comprise a mixture of nucleic acids of different lengths and sequences. Thus, for example, a target element may contain more than one copy of a cloned piece of DNA, and each copy may be broken into fragments of different lengths. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The terms "nucleic acid sample" or "sample of human nucleic acid" as used herein refers to a sample comprising human DNA or RNA in a form suitable for detection by hybridization or amplification. Typically, it will be prepared from a skin tissue sample of a tumor from a patient who has or is suspected of having a melanocytic tumor that may be difficult to classify.

The nucleic acid sample is often be a tissue or cell sample prepared for hybridization using methods described below. The sample is prepared such that individual chromosomes remain substantially intact according to standard techniques. Alternatively, the nucleic acid may be isolated, cloned or amplified. It may be, e.g., genomic DNA, mRNA, or cDNA from a particular chromosome, or selected sequences (e.g. particular promoters, genes, amplification or restriction fragments, cDNA, etc.) within particular amplicons or deletions disclosed here. In some cases, the nucleic acids may be amplified using standard techniques such as PCR. The sample may be isolated nucleic acids immobilized on a solid.

The nucleic acid sample is typically extracted from particular cells, e.g. melanocytes, or prepared from a skin tumor, i. e., a melanocytic neoplasm. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from extracts or supernatants from the cells or the cells themselves from cell cultures, cells from tissue culture and other media in which it may be desirable to detect chromosomal abnormalities, such as changes in copy number. In some cases, the nucleic acids may be amplified using standard techniques such as PCR, prior to the hybridization. The sample may be isolated nucleic acids immobilized on a solid.

The term "probe" or "nucleic acid probe", as used herein, is defined to be a collection of one or more nucleic acid fragments whose specific hybridization to a sample can be detected. The probe may be unlabeled or labeled as described below so that its binding to the target or sample can be detected. The probe is produced from a source of nucleic acids from one or more particular (preselected) portions of a chromosome, e.g., one or more clones, an isolated whole chromosome or chromosome fragment, or a collection of polymerase chain reaction (PCR) amplification products. The probes of the present invention are produced from nucleic acids found in the regions described herein. Often, the probes are centromeric probes, i.e., they hybridize to nucleic acid sequences present in the centromeres of the specific chromosomes, which provide a stronger signal.

The probe or genomic nucleic acid sample may be processed in some manner, e.g., by blocking or removal of repetitive nucleic acids or enrichment with unique nucleic acids. The word "sample" may be used herein to refer not only to detected nucleic acids, but to the detectable nucleic acids in the form in which they are applied to the target, e.g., with the blocking nucleic acids, etc. The blocking nucleic acid may also be referred to separately.

What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767–773; Johnston (1998) *Curr. Biol.* 8: R171–R174; Schummer (1997) *Biotechniques* 23: 1087–1092; Kern (1997) *Biotechniques* 23: 120–124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

A "reference probe" refers to a control probe that specifically hybridizes to a chromosome that does not undergo changes in number in growths that arise from congenital nevi.

"Providing a nucleic acid sample" means to obtain a biological sample for use in the methods described in this invention. Most often, this will be done by removing a sample of cells from an animal, but can also be accomplished by using previously isolated cells (e.g. isolated by another person).

"Tissue biopsy" refers to the removal of a biological sample for diagnostic analysis. In a patient with cancer, tissue may be removed from a tumor, allowing the analysis of cells within the tumor.

DETAILED DESCRIPTION OF THE INVENTION

Figure 1:
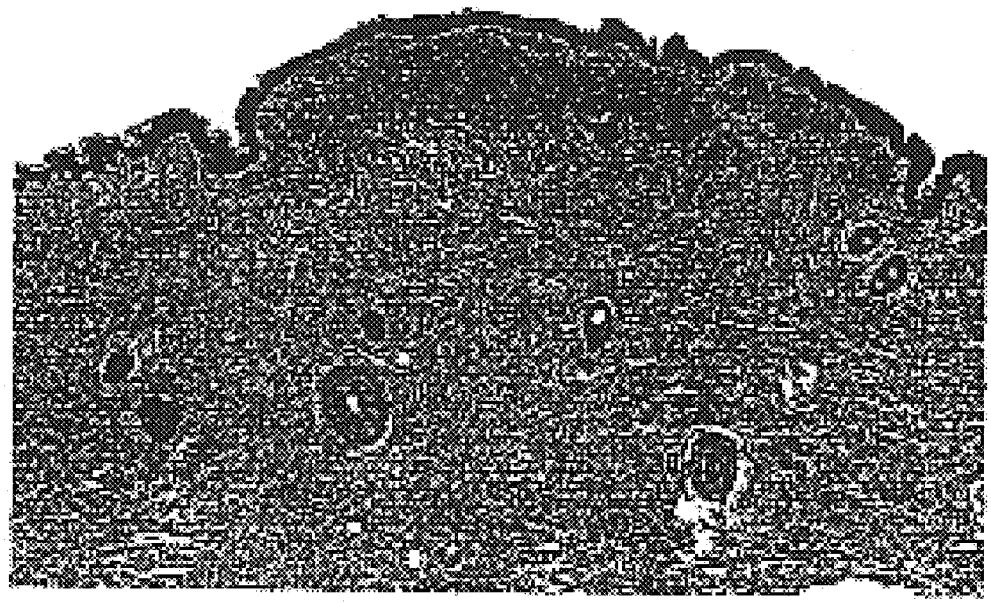
FIG. 1 shows a photomicrograph of case CN12, a representative of group II lesions. In the center of the superficial dermis there is a focus of increased cellularity in an otherwise bland superficial congenital nevus.
Figure 2:
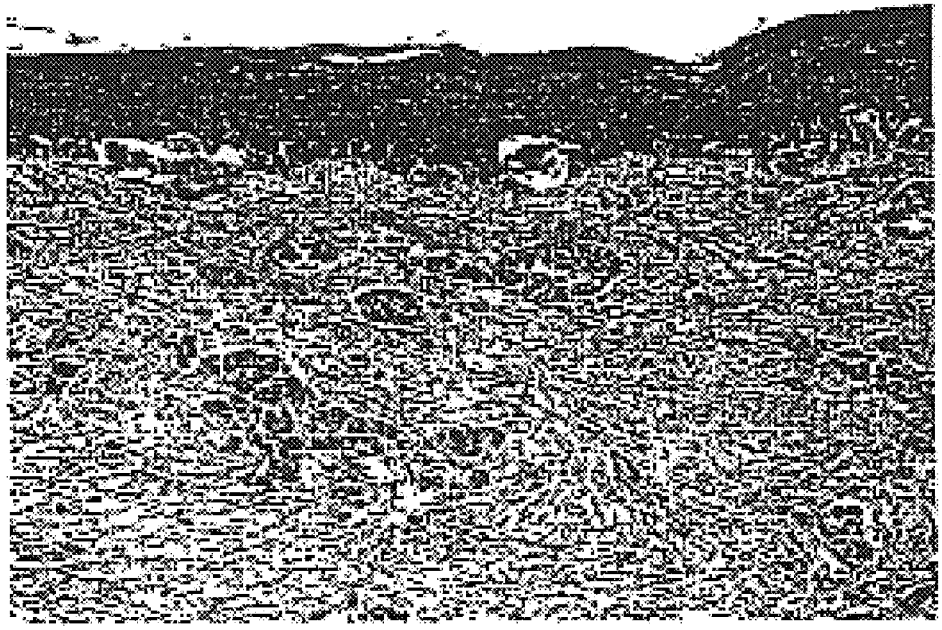
FIG. 2 shows a photomicrograph of CN14, representative of group III, showing a junctional melanocytic proliferation with melanocytes displayed in irregular nests and solitary units, simulating superficial spreading melanoma. This case additionally shows marked desmoplasia and irregularly configured nests of melanocytes in the dermis.
Figure 3:
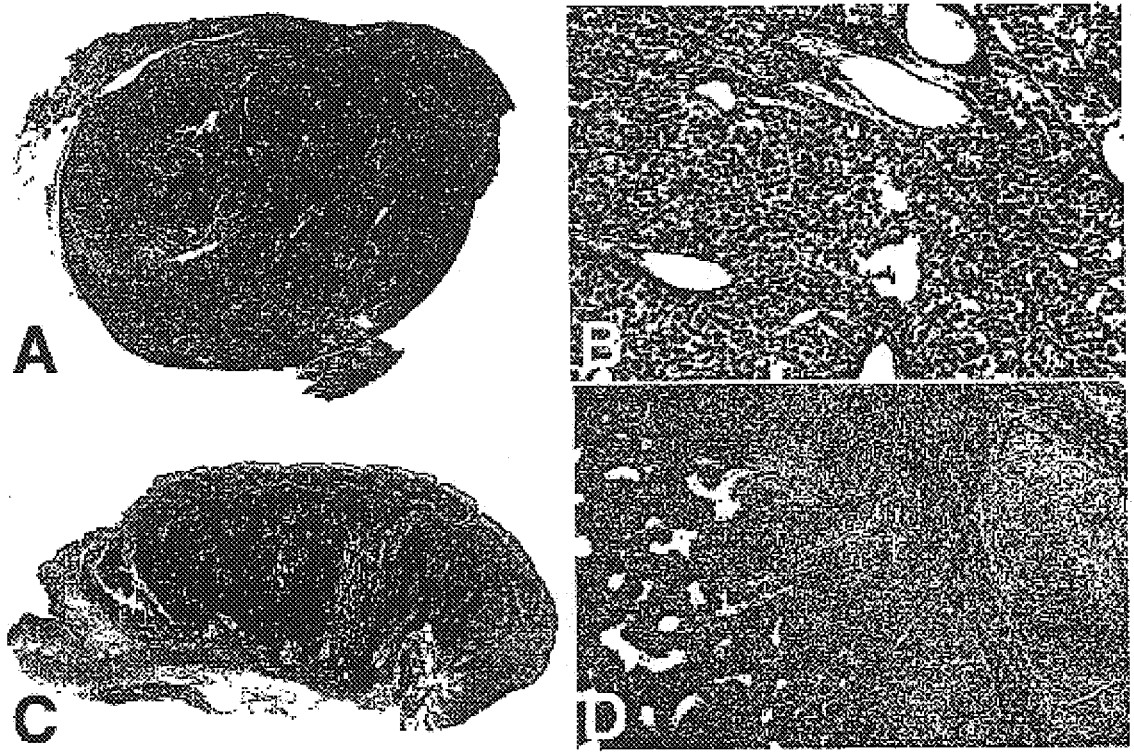
FIG. 3 shows a scanning magnification and close-up of case D62, representative of cases in Group IV (A,B), and case CN10, the only case in group V (C,D). The images show a large, sharply demarcated dermal nodule (a) with increased cellularity and marked angiogenesis (B). A large dermal nodule (c) with areas of increased cellularity and a hemangiopericytoma-like vascular pattern (D, left half), and areas with spindle-shaped cells in a myxoid stroma (D, right half).

The present invention provides methods of typing a growth arising from a congenital melanocytic nevus by detecting (in a sample comprising the growth) the presence of changes in chromosome number that are associated with a benign lesion. Often, the change in chromosome number is a gain of chromosome 10, a gain of chromosome 11, a loss of chromosome 7, or a combination thereof. These changes can also be accompanied by one or more additional changes in chromosome number. Additional changes can include, e.g., a loss of chromosome 5; a gain of chromosome 8, a gain of chromosome 15, a gain of chromosome 20, a gain of chromosome 21, a gain of chromosome 22, a gain of chromosome 16, a loss of chromosome 12, a loss of chromosome 3, a loss of chromosome 5, a loss of chromosome 9, and a loss of chromosome 10 or 11 (when the initial chromosome gain does not involve 10 or 11, respectively).

A benign growth arising from a congenital melanocytic nevus (CMN) can also be identified by detecting an absence of chromosomal aberrations, either numerical or structural, that are frequently associated with melanoma (see, e.g., Bastian et al., *Cancer Res.*, 58:2170–5 (1998); and Bastian, et al., *Cancer Res.*, 60:1968–73 (2000)). Furthermore, a growth arising from a CMN can typically be classified as benign if it contains only changes in whole numbers of chromosomes, which changes do not involve a loss of chromosome 9 or 10, as loss of complete chromosomes as the sole chromosomal aberration(s) is uncommon in melanoma and when it occurs, involves loss of chromsome 9 and/or 10.

General Methods of Measuring Chromosomal Abnormality

Genomic instability is a hallmark of solid tumors, and virtually no solid tumor exists which does not show major alterations of the genome. With the vast majority of tumors this instability is expressed at the level of the chromosomal complement, and thus is detectable by cytogenetic approaches (Mitelman, F., *Catalog of Chromosome Aberrations in Cancer,* 5th Edition (New York: Wiley-Liss) (1994)). However, aneuploidy or chromosomal rearrangement per se is not indicative of malignancy and many benign tumors can have an aberrant karyotype (Mitelman, 1994). To efficiently take advantage of chromosomal abnormalities as a marker, it is mandatory to know characteristic aberrations of the tumors that are to be differentiated.

Several techniques that permit the study of chromosomal complement are well known in the art. For example, fluorescence in-situ hybridization (FISH) can be used to study copy numbers of individual genetic loci or particular regions on a chromosome (Pinkel et al., *Proc. Natl. Acad. Sci. U.S.A.* 85, 9138–42 (1988)). Comparative genomic hybridization (CGH) (Kallioniemi et al. *Science* 258, 818–21 (1992)) may also be used (Houldsworth et al. *Am J Pathol* 145, 1253–60 (1994)) to probe for copy number changes of chromosomal regions as well as changes in chromosome number.

Chromosomal markers of regions that are frequently involved in chromosomal aberrations present in primary melanomas and those associated with benign melanocytic neoplasms that are difficult to distinguish from melanoma are now being developed. These permit the use of hybridization techniques such as FISH and CGH as routine methods to assist in the differential diagnosis of melanoma and a benign melanocytic neoplasm, such as a growth that arises from a congenital nevus.

As appreciated by one of skill in the art, analysis of copy number can be performed using multiple probes to a particular chromosome or can be performed using a single probe, e.g., a centromeric probe, to detect change in copy number. Probes useful in the methods described here are available from a number of sources. For instance, P1 clones are available from the DuPont P1 library (Shepard, et al., *Proc. Natl. Acad. Sci. USA,* 92: 2629 (1994), and available commercially from Genome Systems. Various libraries spanning entire chromosomes are also available commercially (Clonetech, South San Francisco, Calif.), or from the Los Alamos National Laboratory.

In one set of embodiments, the hybridizations are performed on a solid support. For example, probes that selectively hybridize to specific chromosomal regions can be spotted onto a surface. Conveniently, the spots are placed in an ordered pattern, or array, and the placement of the probes on the array is recorded to facilitate later correlation of results. The nucleic acid samples are then hybridized to the array. In one configuration, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606–614; Jackson (1996) *Nature Biotechnology* 14:1685; Chee (1995) *Science* 274: 610; WO 96/17958.

Arrays, particularly nucleic acid arrays can be produced according to a wide variety of methods well known to those of skill in the art (see, e.g., U.S. Pat. No. 6,040,138). For example, in a simple embodiment, "low density" arrays can simply be produced by spotting (e.g. by hand using a pipette) different nucleic acids at different locations on a solid support (e.g. a glass surface, a membrane, etc.).

This simple spotting approach has been automated to produce high density spotted arrays (see, e.g., U.S. Pat. No. 5,807,522). This patent describes the use of an automated systems that taps a microcapillary against a surface to deposit a small volume of a biological sample. The process is repeated to generate high density arrays. Arrays can also be produced using oligonucleotide synthesis technology. Thus, for example, U.S. Pat. No. 5,143,854 and PCT patent publication Nos. WO 90/15070 and 92/10092 teach the use of light-directed combinatorial synthesis of high density oligonucleotide arrays.

In another embodiment the array, particularly a spotted array, can include genomic DNA, e.g. overlapping clones that provide a high resolution scan of the amplicon corresponding to the region of interest. Amplicon nucleic acid can be obtained from, e.g., MACs, YACs, BACs, PACs, P1s, cosmids, plasmids, inter-Alu PCR products of genomic clones, restriction digests of genomic clone, cDNA clones, amplification (e.g., PCR) products, and the like.

In various embodiments, the array nucleic acids are derived from previously mapped libraries of clones spanning or including the target sequences of the invention, as well as clones from other areas of the genome, as described below. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

Target elements of various sizes, ranging from 1 mm diameter down to 1 $\mu$m can be used. Smaller target elements containing low amounts of concentrated, fixed probe DNA are used for high complexity comparative hybridizations since the total amount of sample available for binding to each target element will be limited. Thus it is advantageous to have small array target elements that contain a small amount of concentrated probe DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup, *Cytometry* 16: 206–213, 1994).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, the samples can be placed in separate wells or chambers and hybridized in their respective well or chambers. The art has developed robotic equipment permitting the automated delivery of reagents to separate reaction chambers, including "chip" and microfluidic techniques, which allow the amount of the reagents used per reaction to be sharply reduced. Chip and microfluidic techniques are taught in, for example, U. S. Pat. No. 5,800,690, Orchid, "Running on Parallel Lines" New Scientist, Oct. 25, 1997, McCormick, et al., *Anal. Chem.* 69:2626–30 (1997), and Turgeon, "The Lab of the Future on CD-ROM?" *Medical Laboratory Management Report*. Dec. 1997, p.1. Automated hybridizations on chips or in a microfluidic environment are contemplated methods of practicing the invention.

Although microfluidic environments are one embodiment of the invention, they are not the only defined spaces suitable for performing hybridizations in a fluid environment. Other such spaces include standard laboratory equipment, such as the wells of microtiter plates, Petri dishes, centrifuge tubes, or the like can be used.

In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids.

In some applications it is necessary to block the hybridization capacity of repetitive sequences. Thus, in some embodiments, human genomic DNA or Cot-1 DNA is used to block non-specific hybridization.

In Comparative Genomic Hybridization (CGH) methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Hybridization protocols suitable for use with the methods of the invention are described, e.g., in Albertson (1984) *EMBO J.* 3: 1227–1234; Pinkel (1988) *Proc. Natl. Acad. Sci. USA* 85: 9138–9142; EPO Pub. No. 430,402; *Methods in Molecular Biology*, Vol. 33: *In Situ Hybridization Protocols*, Choo, ed., Humana Press, Totowa, N.J. (1994), etc. In some embodiments, the hybridization protocol of Pinkel et al. (1998) *Nature Genetics* 20:207–211 or of Kallioniemi (1992) *Proc. Natl Acad Sci USA* 89:5321–5325 (1992) is often used.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.1 to about 0.5 mg/ml DNA (e.g., cot-1 DNA). The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology*, Vol. 24: *Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background membranes can be used (see, e.g., Chu (1992) *Electrophoresis* 13:105–114). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Other nucleic acid hybridization formats are also known to those skilled in the art. Such formats are described, for example in Sambrook and Russell, supra. These includes analyses such as southern blotting. The sensitivity of the hybridization assays may also be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Ploidy, i.e., chromosome number, may also be determined using quantitative PCR such as real-time PCR (see, e.g., Suzuki et al., *Cancer Res.* 60:5405–9 (2000)). For example, quantitative microsatellite analysis (QuMA) can be performed for rapid measurement of relative DNA sequence copy number. In QuMA, the copy number of a test locus relative to a pooled reference is assessed using quantitative, real-time PCR amplification of loci carrying simple sequence repeats. Use of simple sequence repeats is advantageous because of the large numbers that are mapped precisely.

Additional protocols for quantitative PCR are provided in Innis et al. (1990) PCR Protocols, A Guide to Methods and Applications, Academic Press, Inc. N.Y.).

Labeling and Detection of Nucleic Acids

The hybridized nucleic acids are typically detected by detecting one or more labels attached to the sample or probe nucleic acids. The labels may be incorporated by any of a number of means well known to those of skill in the art. Means of attaching labels to nucleic acids include, for example nick translation or end-labeling (e.g. with a labeled RNA) by kinasing of the nucleic acid and subsequent attachment (ligation) of a nucleic acid linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence. Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. The nucleic acid probe may also be labeled with digoxigenin and then detected with an antibody that is labeled with a fluorochrom, or an enzyme such as horseradish peroxidase or alkaline phosphatase. For a detailed review of methods of labeling nucleic acids and detecting labeled hybridized nucleic acids see *Laboratory Techniques in Biochemistry and Molecular Biology*, Vol. 24: *Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

Kits for Use in Diagnostic and/or Prognostic Applications

Kits for use in diagnostic, research, and prognostic applications are also provided by the invention. Such kits may include any or all of the following: assay reagents, buffers, nucleic acids for detecting the target sequences and other hybridization probes and/or primers. The kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example shows the identification of changes in chromosome number associated with growths arising from congenital nevi.

Cases: Formalin-fixed, paraffin-embedded biopsies from congenital giant nevi of 23 patients were retrieved from the archives of the Department of Pathology, University of California at San Francisco or obtained from cases sent for consultation. All nodular proliferations were from infants 2 days to 4 months old. The patient's age ranged from one day to 20 years, the average and median ages were 3.5 and 0.3 years. The cases were assigned to one of five histological groups according to the predominant histological pattern (tables 1 and 2). Two cases of bona fide melanoma that arose in congenital nevi of two adults, a 41 year-old female, and a 59-year old male, were also studied and were assigned to group VI.

Cases of CMN and CMN with secondary proliferations were assigned to groups according to the predominant histological pattern: I) bland congenital nevi (n=6); II) congenital nevi with foci of increased cellularity (n=4); III) CMN with a proliferation simulating superficial spreading melanoma in situ (n=3); IV) CMN with a proliferation simulating nodular melanoma (n=9); V) proliferating neurocristic hamartoma (n-1); VI) melanoma arising in congenital nevus (n=2). No aberrations were found in groups I–III, whereas 7/9 cases of group IV, and 1/1 case of group V, showed aberrations.

As a comparison, a group of 122 primary cutaneous melanomas that had been previously analyzed by CGH, some of which have been previously published (Bastian, B. C. et al., *Cancer Res.*, 58:2170–5 (1998); Bastian, B. C. et al., *Cancer Res.*, 60:1968–73 (2000)), was used.

Comparative genomic hybridization was performed as follows:

DNA Extraction Tissue for CGH analysis was selectively microdissected from regions of highest cellular density that were most representative of the particular histologic group. Tumor-bearing tissue was microdissected from 30 µm sections (2 to 20 per tumor) using hematoxylin-eosin stained sections as guidance. DNA extraction and labeling was performed as published earlier (Bastian, B. C. et al., *Cancer Res.*, 58:2170–5 (1998)).

All CGH measurements were performed in duplicates: once with 1 µg tumor DNA labeled with fluorescein-12-dUTP (Dupont Inc., Boston, Mass.), and 200 ng Texas red-5-dUTP labeled reference DNA ("standard" labeling), and a second time with the labeling reversed.

Controls and Threshold Definitions Normal DNA and DNA from tumor cell lines with known aberrations were used as negative and positive controls for CGH, respectively. A region was considered as aberrant when 1) either the standard labeling or the reverse labeling resulted in a tumor/reference fluorescent ratios <0.80 or >1.2 or 2) both the standard and the reverse labeling resulted in a tumor: reference fluorescent ratios <0.85 or >1.15 (Bastian, B. C. et al., *Cancer Res.*, 58:2170–5 (1998)).

Immunohistochemistry was performed as follows:

Proliferation was assessed using an antibody against Ki-67 (Mib-1, Beckman Coulter, Fullerton, Calif., dilution 1:500) according to the manufacturer's instructions. Immunoreactivity was assessed using the 20× objective and only cells that showed definitive nuclear staining were counted.

Results

None of the 13 cases (0%) of groups I–III showed any chromosomal aberrations by CGH whereas 7/9 (78%) of the cases of group IV, and 1/1 (100%) of group V showed aberrations. The predominant pattern in the cases of group IV was gain or loss of entire chromosomes only. This differs from the aberration pattern observed in melanoma (Bastian, B. C. et al., *Cancer Res.*, 58:2170–5 (1998); Bastian, B. C. et al., *Cancer Res.*, 60:1968–73 (2000)), in which most cases have aberrations involving only partial chromosomes (table 2). In group IV, 6/9 cases (67%) showed numerical aberrations of whole chromosomes exclusively, differing significantly from the findings in melanoma arising within CMN (n=2) or independent of CMN (n=122) in which only 5% showed numerical changes only. The single case in group VI showed aberrations similar to melanoma.

In a total of 108 melanomas that were studied by CGH and in which aberrations were detected, 102 (95%) showed at least one aberration that involved a fraction of a chromosome. By contrast, only one of the seven lesions (14%) of group IV that showed an aberration involved a partial chromosome. This case had a gain of chromosome 6p as the single aberration present. The remaining six cases with aberrations only showed gains or losses involving whole chromosomes.

In addition to the difference in aberration pattern there were also differences in the specific chromosomes involved. In the melanomas with aberrations involving whole chromosomes only (6 out of a total of 122), chromosomes 9 or 10 were always involved. Indeed, these losses are the most frequent cytogenetic change in primary cutaneous melanoma, occurring in about 60% of all cases. In the cases of group IV, however, losses of chromosomes 9 and 10 were less frequent. Only one case (14%) had loss of 9, and two (20%) cases had loss of 10.

There were additional differences in the aberration patterns between the group IV and melanoma cases. Loss of chromosome 7, which was seen in three group IV cases, gain of chromosome 11, which was seen in one Group IV case, and gain of chromosome 10, which was seen in one Group IV case, were never observed in any melanoma cases analyzed to date. Only the case showing features previously described as proliferative neurocristic hamartoma (group V) (Clark, W. H. et al., *Pathology of the Skin,* 1st edition, pp. 729–35, New York, McGraw-Hill (1990)) and the two cases of melanoma arising in congenital nevi showed multiple cytogenetic aberrations in a pattern indistinguishable from the melanomas not arising in the context of a congenital nevus (table 2). There were multiple aberrations that frequently involved chromosomal fragments. Moreover, loss of chromosome 9 was present in all three cases.

One patient of group III died of her CMN. No autopsy data and documentation on whether metastatic spread had occurred was available. The last records showed severe intestinal obstruction due to perianal obstruction. None of the biopsies showed evidence of melanoma. Clinical follow-up information of 5 cases of group 4 (mean follow-up time 1.6 years) did not show any progression to melanoma (table 2). One of the patients of group VI died of metastatic melanoma.

Consistent with the marked increase in mitotic rate the cases of Group III, IV, and V the Ki-67 labeling index was increased in these cases (table 2). Nine of ten group IV cases (80%) had a proliferative index of 5% or above, whereas only 1/10 cases of groups had a labeling rate over 1%.

This example shows that frequent chromosomal aberrations in atypical nodular proliferations arise in congenital nevi. These results differ from a previous report of two nodular proliferations, which were normal by conventional cytogenetic analysis (Mancianti, M. L. et al., *Am J Pathol.*, 136:817–29 (1990)). This may be due the necessity of subculturing for cytogenetic analysis with the potential risk of expanding a non-relevant clone or simply by the small number of cases in this study. The ability of CGH to detect these changes suggests that identical aberrations were present in the majority of cells of the lesions, and implies that these lesions were clonal.

The pattern of the aberrations that were identified in the atypical nodular proliferations of group IV differs from those found primary cutaneous melanoma (Bastian, B. C. et al., *Cancer Res.*, 58:2170–5 (1998); Bastian, B. C. et al., *Cancer Res.*, 60:1968–73 (2000)). Seven out of nine (78%) of the atypical nodular proliferations in group IV with aberrations detected by CGH had involvement of whole chromosomes only, whereas this pattern was seen in only 5% of over 100 melanomas. By contrast, 95% of melanomas with aberrations show one or several gains or losses of chromosomal fragments. These findings indicate that the type of genomic instability in atypical nodular proliferations may differ from that predominating in melanoma.

Not to be bound by theory, defects that permit numerical chromosomal aberrations may result in a less malignant phenotype, as compared to those that promote structural aberrations, as whole chromosomes are likely to harbor some genes that provide a growth advantage along with others that inhibit growth. In contrast, cancers bearing only the fragment carrying the advantageous genes are freed from the normally present growth inhibiting genes on the same chromosome and would be likely to grow faster. The degree of genomic instability would increase the plasticity of the genome and permit a rapid evolution of the hallmarks of cancer (Hanahan, D. and Weinberg, R. A., *Cell*, 100:57–70 (2000)). Tumors with a more rigid genome, such as those that permit only a change in chromosome numbers, would undergo a slower progression or may not be able to acquire all features of malignancy before they undergo replicative senescence and halt progression.

The numerical aberrations in the atypical nodular proliferations position them in the spectrum between benign melanocytic nevi that tend to have no chromosomal aberrations and outright melanoma in which both numerical and structural aberrations are the rule. The aberration pattern in the atypical nodular proliferations points towards a malfunction in chromosomal segregation, such as within the mitotic spindle checkpoint (Amon, A., *Curr Opin Genet Dev.*, 9:69–75 (1999)). By contrast, only the case with features of a proliferative neurocristic hamartoma showed multiple chromosomal aberrations that involved chromosome fragments, indistinguishable from melanoma. However, this patient was alive and free of any signs of malignancy after 15 years.

In summary, these data show frequent chromosomal aberrations in atypical nodular proliferations arising in congenital nevi. The aberrations differ from those seen in melanoma in the type of aberrations (numerical aberrations in atypical nodular proliferations versus structural aberrations in melanoma) and 2) the pattern of chromosomes involved (losses of chromosome 7 in atypical nodular proliferations, and frequent losses of chromosomes 9 and 10 in melanoma). These data indicate fundamental differences relative to melanoma and can be used to classify ambiguous cases.

TABLE 1

Histological definition of groups I–VI

| | |
|---|---|
| Group I | Congenital nevus, superficial or deep type |
| Group II | Congenital nevus, superficial or deep type, with superficial dermal foci of increased cellularity |
| Group III | Congenital nevus, superficial or deep type, with marked intraepidermal upward scatter and large junctional nests of melanocytes simulating superficial spreading melanoma |
| Group IV | Congenital nevus, superficial or deep type, with nodular proliferations of high cellularity, nuclear atypia, and markedly increased proliferation rate |
| Group V | Features of proliferative neurocristic hamartoma with nests of epitheloid melanocytes surrounded by a loose myxoid stroma with spindle cells |
| Group VI | Melanoma arising in a congenital nevus |

TABLE 2

Summary of clinical, histological, and genetic findings of cases. The definition of histological groups is shown in table 1. Dim indicate losses, enh indicates gains (Basel, S., Karger ISCN (1995): An International System for Human Cytogenetic Nomenclature (1995)).

| Case | Age | Sex | Clinical | Histology* | CGH | Ki67 | Follow-up |
|---|---|---|---|---|---|---|---|
| CN28A | 5 years | f | Large CMN on right face | I | no changes | 1% | 5.5 years |
| CN25 | 5 months | f | Large CMN on buttock, abdomen, scalp and ear | I | no changes | 1% | 5.5 years |
| CN2 | 20 years | f | Intermediate CMN on lower leg | I | no changes | <1% | N/A |
| CN3 | 15 years | m | Intermediate CMN on upper back | I | no changes | <1% | N/A |
| CN4 | 20 years | f | Small CMN on chin | I | no changes | <1% | N/A |
| CN1 | 13 years | m | Small CMN on left flank | I | no changes | 5% | N/A |
| CN26 | 1 years | f | Intermediate CMN on left hand | II | no changes | 1% | 2 years |
| CN12 | 7 months | m | Large CMN on back, trunk, left arm | II | no changes | 1% | 2.5 years |
| CN17 | 2 years | f | Large CMN on scalp | II | no changes | 1% | 3 years |
| CN11/1 | 3 months | f | Large CMN on trunk, centered over LS spine, extending onto right thigh; Multiple satellites; Grey-blue color, multinodular and infiltrated pattern; congenital erosion | II | no changes | N.D. | 5 years |
| CN19 | 10 months | f | Large CMN with segmental pattern right groin and buttock onto leg; Very dark at birth but lightened, but with marked irregular specks and mottling | III | no changes | 1% | 4 years |
| D122 | 1 days | m | Large, atypical appearing CMN19 × 10 cm centered on R chest; Stellate ~6.5 × 4 cm "scar like area" in center | III | no changes | 8% | 9 months |
| CN14 | 7 months | f | Large CMN involving back, buttock and perineum; Recent growth with perirectal involvement and consecutive obstruction | III | no changes | 5% | Died of disease. No autopsy data available |
| CN16 | 4 months | f | Large CMN on scalp with a firm nodule in the central portion | IV | dim (5) | 10% | 4 years |
| CN22 | 3 months | f | Large CMN on upper back with a papular growth | IV | enh (8, 15, 20, 21) dim (10) | 5% | N/A |
| CN24 | 2 days | m | Large CMN on entire lower back | IV | no changes | | N/A |
| D140 | 1.5 months | f | Large CMN covering trunk, groin and thighs, with satellites, irregular colors; Multiple papules and vascular-nodules at time of biopsy | IV | enh (10, 11, 16, 20, 22) dim (12) | 5% | 1 year |
| D32 | 2 days | f | Large CMN with bathing suit like distribution | IV | dim (3, 5, 7, 9, 11) enh (20) | 8% | 2.5 years |
| D62 | 2 months | f | CMN with occipital scalp | IV | no changes | 5% | N/A |

TABLE 2-continued

Summary of clinical, histological, and genetic findings of cases. The definition of histological groups is shown in table 1. Dim indicate losses, enh indicates gains (Basel, S., Karger ISCN (1995): An International System for Human Cytogenetic Nomenclature (1995)).

| Case | Age | Sex | Clinical | Histology* | CGH | Ki67 | Follow-up |
|---|---|---|---|---|---|---|---|
| D146 | 4 months | m | Large CMN on abdomen | IV | dim (7, 10) enh (8) | 10% | N/A |
| CN29 | 3 months | f | Large CMN on left leg extending onto perineum and buttocks with multiple satellite lesions; Clinically extreme variability with flesh colored and reddish nodules, black macules on leg | IV | dim (7) | 5% | 1.5 years |
| CN30 ½ | 16 days | f | Large CMN on buttocks with recent bleeding pigmented plaque on right buttock and proliferating nodules inguinal area | IV | enh (6p) | 7% | 2 months |
| CN10 | 3 days | f | Large CMN on posterior trunk | V | dim (3, 4, 5p, 9pter-9q21, 18) enh (2pter-p13, 2q32-qter, 6p, 6q24-qter, 7, 8, 15q21-15qter, 16q21-qter, 20) | 7% | 15 years |
| D168 | 59 years | m | Nodule arising in a small CNM | VI | dim (04pter-04qter, 9, 12q14-qter) enh (7, 8, 9q34-qter, 11q13-11q13, 19, 20) | N.D. | N/A |
| CN31 | 42 years | f | Nodule arising in a large CNM on buttocks | VI | dim (1p, 2, 5cen-q32, 6cen-q22, 9, 13) | N.D. | Died of metastatic melanoma |

TABLE 3

Comparison of chromosomal aberrations in proliferative nodules arising in CMN (groups IV and V) and those in primary cutaneous melanoma. Dim stands for loss (Basel, S., Karger ISCN (1995): An International System for Human Cytogenetic Nomenclature (1995)).

| | n | Loss of 9 | Loss of 10 | Loss of 7 | Whole chromosomes | Partial chromosomes |
|---|---|---|---|---|---|---|
| Proliferative nodules in CMN | 10 | 2 (20%) | 2 (20%) | 3 (30%) | 6 (60%) | 2 (25%) |
| Primary cutaneous melanoma | 122 | 73 (60%) | 71 (58%) | 0 (0%) | 6 (5%) | 110 (90%) |

What is claimed is:

1. A method of typing a proliferative nodule in a congenital melanocytic nevus as a benign growth, the method comprising providing a nucleic acid sample from the nodule and detecting a loss of whole chromosome 7 thereby typing the nodule as a benign growth.

2. The method of claim 1, further comprising detecting a gain or loss of another whole chromosome.

3. The method of claim 1, wherein the detecting step comprises:
   contacting a nucleic acid sample from the patient with a probe which selectively hybridizes to a target polynucleotide sequence chromosome 7; wherein the probe is contacted with the sample under conditions in which the probe binds selectively with the target polynucleotide sequence to form a stable hybridization complex; detecting the formation of the hybridization complex; and detecting a loss of whole chromosome 7.

4. The method of claim 1 wherein the detecting step comprises an amplification reaction.

5. The method of claim 4, wherein the amplification reaction is a polymerase chain reaction.

6. The method of claim 3, wherein the probe is a centromeric probe.

7. The method of claim 1, wherein the nucleic acid sample is an interphase nucleus.

8. The method of claim 1, wherein the nucleic acid sample is a metaphase cell.

9. The method of claim 3, wherein the probe is labeled with a fluorescent label.

10. The method of claim 3, wherein the probe is labeled with digoxigenin or biotin.

11. The method of claim 3, further comprising the step of blocking the hybridization capacity of repetitive sequences in the nucleic acid sample.

12. The method of claim 11, wherein unlabeled blocking nucleic acids comprising repetitive sequences are contacted with the sample.

13. The method of claim 12, wherein the unlabeled blocking nucleic acids are Cot-1 DNA.

14. The method of claim 3, wherein the probe is bound to a solid substrate.

15. The method of claim 14, the probe is a member of an array.

* * * * *